United States Patent
Arai et al.

(10) Patent No.: US 9,636,478 B2
(45) Date of Patent: May 2, 2017

(54) MEDICAL TUBE

(71) Applicants: NATIONAL CANCER CENTER, Tokyo (JP); PIOLAX MEDICAL DEVICES, INC., Yokohama-shi (JP)

(72) Inventors: Yasuaki Arai, Tokyo (JP); Shinichi Sakai, Yokohama (JP); Yuuki Inami, Yokohama (JP)

(73) Assignees: NATIONAL CANCER CENTER, Tokyo (JP); PIOLAX MEDICAL DEVICES, INC., Yokohama-Shi, Kanagawa (JP)

( * ) Notice: Subject to any disclaimer, the term of this patent is extended or adjusted under 35 U.S.C. 154(b) by 42 days.

(21) Appl. No.: 14/779,277

(22) PCT Filed: Mar. 27, 2013

(86) PCT No.: PCT/JP2013/059068
§ 371 (c)(1),
(2) Date: Sep. 22, 2015

(87) PCT Pub. No.: WO2014/155576
PCT Pub. Date: Oct. 2, 2014

(65) Prior Publication Data
US 2016/0074622 A1 Mar. 17, 2016

(51) Int. Cl.
*A61M 1/00* (2006.01)
*A61M 5/00* (2006.01)
(Continued)

(52) U.S. Cl.
CPC ....... *A61M 25/0075* (2013.01); *A61M 27/002* (2013.01); *A61M 27/006* (2013.01); *A61M 2025/0078* (2013.01)

(58) Field of Classification Search
CPC ...... A61M 2025/0078; A61M 25/0075; A61M 27/002; A61M 27/006
(Continued)

(56) References Cited

U.S. PATENT DOCUMENTS 4,549,879 A * 10/1985 Groshong ......... A61M 25/0075
604/247
4,737,152 A 4/1988 Alchas
(Continued)

FOREIGN PATENT DOCUMENTS

EP 0 250 891 A1 1/1988
EP 0 613 696 A1 9/1994
(Continued)

OTHER PUBLICATIONS

English-language translation (1 page) of International Preliminary Examination Report (IPER) in PCT/JP2013/059068 dated Apr. 28, 2015.
(Continued)

*Primary Examiner* — Jason Flick
(74) *Attorney, Agent, or Firm* — McGinn IP Law Group, PLLC

(57) ABSTRACT

A medical tube, which is inserted into a tubular organ and discharges and suctions fluid, is provided with a tube-shape main body which extends a prescribed length and with a valve which is disposed in a portion of the main body that is inserted into the tubular organ and can discharge or suction a fluid, wherein the valve includes multiple slits which are formed so as to extend axially of the body a prescribed length, reaching from the outer periphery to the inner periphery of the main body, and which are provided spaced in the circumferential direction of the main body.

(Continued)

Each slit is formed tilted in the same direction with respect to a radially-extending line which passes through the axial center of the main body.

3 Claims, 12 Drawing Sheets

(51) Int. Cl.
*A61M 25/00* (2006.01)
*A61M 27/00* (2006.01)

(58) Field of Classification Search
USPC .......................................................... 604/31
See application file for complete search history.

(56) References Cited

U.S. PATENT DOCUMENTS

| | | | | |
|---|---|---|---|---|
| 4,995,863 | A | * | 2/1991 | Nichols ............... A61M 25/003 604/247 |
| 5,807,349 | A | * | 9/1998 | Person .............. A61M 25/0075 604/247 |
| 5,810,789 | A | | 9/1998 | Powers et al. |
| 2002/0156430 | A1 | * | 10/2002 | Haarala ............. A61M 25/0075 604/247 |
| 2011/0054415 | A1 | | 3/2011 | Onuma et al. |

FOREIGN PATENT DOCUMENTS

| | | |
|---|---|---|
| JP | S60-58167 A | 4/1985 |
| JP | S63-24958 A | 2/1988 |
| JP | 2011-050420 A | 3/2011 |
| JP | 2012-200304 A | 10/2012 |
| WO | WO 02/085439 A2 | 10/2002 |
| WO | WO 2011/093131 A1 | 8/2011 |

OTHER PUBLICATIONS

English-language translation (2 pages) of International Preliminary Examination Report (IPER) in PCT/JP2013/059068 dated Jul. 28, 2015.
Extended European Search Report dated Nov. 15, 2016.
International Search Report (ISR) (PCT Form PCT/ISA/210), in PCT/JP2013/059068, dated Jun. 25, 2013.
International Preliminary Examination Report in PCT/JP2013/059068 dated Apr. 28, 2015.
International Preliminary Examination Report in PCT/JP2013/059068 dated Jul. 28, 2015.

* cited by examiner

MEDICAL TUBE

TECHNICAL FIELD

The present invention relates to a medical tube such as a catheter which is to be indwelled in a blood vessel to administer a medical solution such as an anticancer agent, a shunt tube for draining a fluid accumulated in the brain ventricle into the abdominal cavity, or a drainage tube which is to be inserted into the bile duct or the like to drain the bile or the like.

BACKGROUND ART

To inject a medical solution such as an anticancer agent into the main body, for example, a catheter is percutaneously inserted into a tubular organ such as a blood vessel. Thereafter, its tip end portion is moved to reach the cancer-affected portion, and the medical solution is administered from a discharge hole disposed in the tip end portion. Alternatively, the tip end of a catheter is moved to reach a central vein, and the medical solution is administered to the whole body is performed. This kind of catheter may be provided with a valve element at a discharge hole, in order to prevent the blood or the like from reversely flowing into the catheter to coagulate therein. The valve element opens when a medical solution or the like is administered, and closes in other cases is sometimes disposed.

In recent clinical practice, in order to check whether a tip end portion of a catheter is placed in a blood vessel or not, a suction work of sucking blood from the tip end portion of the catheter may be required to thereby check whether the blood flows out from the base end side of the catheter or not (ONS Guidelines etc.). In order to perform the suction work, there is used a catheter also having a suction valve element.

As this kind of catheter, Patent Literature 1 describes a valved catheter in which an injection hole is provided with a slit valve, and a suction hole is a provided with a flap valve. The slit valve is provided by forming a linear slit in a peripheral wall portion of the catheter. The flap valve is provided by forming an arcuate slit in the peripheral wall portion. In the catheter, when a medical solution is injected into the interior and pressurized, the slit valve opens and the medical solution is injected into a blood vessel through the injection hole. On the other hand, when the interior is depressurized, the flap valve opens, and the blood is sucked into the catheter through the suction hole.

There is also known a catheter including a so-called two-way valve. In this kind of catheter, instead of providing valve elements respectively for discharge and suction as in the above-described valved catheter, the valve is configured to open both in the case where a medical solution or the like is to be discharged, and in the case where the blood or the like is to be sucked.

For example, Patent Literature 2 describes a valved catheter in which a valve including an openable slit is formed in the longitudinal direction in the distal-end side of a pipe main body having a circular cross-sectional shape. One of both edge portions of the slit of the valve is made to be easily deformable than the other edge portion when a fluid is passed from the interior to the exterior through the valve and when a fluid is passed from the exterior to the interior through the valve. In this kind of catheter, when the interior is pressurized or depressurized, the one edge portion of the slit which is more easily deformable is deformed, whereby the slit is caused to open, and a medical solution is discharged or the blood is sucked.

CITATION LIST

Patent Literature

Patent Literature 1: JP-A-2012-200304-A
Patent Literature 2: JP-A-2011-50420-A

SUMMARY OF INVENTION

Technical Problem

In the valved catheter of Patent Literature 1, the valve elements are disposed respectively for discharge and suction. However, it is difficult to dispose the plural valve elements in a limited space. If the portion in which the flap valve is disposed abuts against the inner wall of the blood vessel, even when the flap valve is caused to open by depressurizing the interior of the catheter, the suction hole is closed by the inner wall of the blood vessel. Thus, the blood might not be effectively sucked into the catheter.

On the other hand, in the valved catheter of Patent Literature 2, since one of both edge portions of the slit is required to be more easily deformable than the other edge portion, it is difficult to process the slit.

It is an object of the invention to provide a medical tube in which discharge of a fluid such as a medical solution, and suction of a fluid such as the blood are enabled to be surely performed, by a relatively simple structure.

Solution to Problem

In order to attain the object, the invention provides
a medical tube which is to be inserted into a tubular organ or a body cavity to discharge or suck a fluid, including:
a tubular main body which extends by a predetermined length; and
a valve which is disposed in a portion of the main body, the portion being to be inserted into the tubular organ or the body cavity, and which is configured to discharge or suck the fluid,
wherein the valve is configured by plural slits which extend by a predetermined length in an axial direction of the main body, which are formed so as to extend from an outer circumference of the main body to an inner circumference, and which are disposed at intervals in a circumferential direction of the main body, and
wherein the slits are formed to be inclined in a same direction with respect to a line L that passes through an axial center C of the main body and that extends in a radial direction.

The invention may preferably provide the above-mentioned medical tube,
wherein angles θ of the slits with respect to the line L of the main body are 10 to 60°.

The invention may preferably provide the above-mentioned medical tube,
wherein R/T is 2 to 6, where an inner diameter of the main body is R and a thickness of the main body along the line L is T.

The invention may preferably provide the above-mentioned medical tube,
wherein axial lengths S of the slits are 1.6 to 5.0 times an outer diameter D of the main body.

The invention may preferably provide the above-mentioned medical tube,
wherein axial angles E of the slits with respect the axial center C of the main body are ±6°.

Advantageous Effects of Invention

According to the invention, when a medical solution such as an anticancer agent or a nutrient is injected into the medical tube, and the interior of the main body is pressurized, wall portions of the main body which are separated from each other through the plural slits are pressed toward the outer diameter side of the main body, whereby the slits are caused to open. Therefore, the fluid can be discharged.

On the other hand, when the interior of the medical tube is sucked and depressurized by a pump, a syringe, or the like, the wall portions of the main body which are separated from each other by the slits bend toward the inner diameter side of the main body. As a result, end portions which are butted against each other through the slits are strongly pressed against each other.

In this case, the slits are formed to be inclined in the same direction with respect to the line L that passes through the axial center C of the main body and that extends in a radial direction. Therefore, one of the end portions which are butted against each other through the slit intersects at an acute angel with the inner circumferential surface, and at an obtuse angle with the outer circumferential surface (hereinafter, the end portion is referred to as "inner end portion"). The other one of the end portions which are butted against each other through the slit intersects at an obtuse angel with the inner circumferential surface, and at an acute angle with the outer circumferential surface (hereinafter, the end portion is referred to as "outer end portion").

When, as described above, the end portions which are butted against each other through the slit are strongly pressed against each other by the suction of the interior of the medical tube, slippage occurs between the inclined slit surfaces, the inner end portion is moved toward the inner diameter side of the medical tube, and the outer end portion is moved toward the outer diameter side of the medical tube. Therefore, the peripheral wall portions which are divided by the plural slits are moved in the inclination direction of the slits (in the direction in which the tip ends formed by the slits form an acute angle), the end portions which are butted against each other through the slits are disengaged from each other, and the slits largely open. Consequently, a fluid which exists outside the medical tube, such as a body fluid can be effectively sucked.

In the medical tube, the valve is configured by the plural slits which are disposed at intervals in the circumferential direction of the main body. In the case where the main body is inserted into a tubular organ or a body cavity, even when a portion of the main body in the circumferential direction abuts against the inner wall of the tubular organ or the body cavity, and the slit(s) in the portion is closed, therefore, the other slit(s) opens, and therefore a fluid can be surely sucked into the main body. The plural slits are disposed at intervals in the circumferential direction of the main body. In the above-described operations of discharging or sucking a fluid, therefore, the pressing force caused by the fluid, or the suction force caused by a syringe or the like acts in a balanced manner on the inner surfaces of the wall portions. Therefore, the wall portions are caused to easily deform, and the slits are enabled to easily open.

According to the invention, as described above, it is possible to provide a medical tube in which discharge of a fluid such as a medical solution, and suction of a fluid such as a body fluid are enabled to be surely performed, simply by forming a plural slits to be inclined in the same direction with respect to the line L that passes through the axial center C of the main body and that extends in an radial direction, at intervals in the circumferential direction of the main body.

BRIEF DESCRIPTION OF DRAWINGS

FIG. 2A is an enlarged side view of main portions. FIG. 2B is an enlarged front view of main portions. FIG. 2C is a sectional view taken along arrow lines B-B in FIG. 2B.

FIG. 4A is an enlarged sectional view of main portions in a state where slits have not yet opened. FIG. 4B is a sectional view of main portions in a state where the slits open.

FIG. 6A is a sectional view of main portions in the initial state where a pressing force is applied to the slits. FIG. 6B is a sectional view of main portions in a state where end portions which are butted against each other through the slits begin to be displaced. FIG. 6C is a sectional view of main portions in a state the portions which are butted against each other through the slits are displaced from each other, the slits open, and the fluid is sucked.

FIG. 10A is a sectional view of main portions in a normal state. FIG. 10B is a sectional view of main portions in a state where a fluid is discharged. FIG. 10C is a sectional view of main portions in a state where a fluid is sucked.

FIG. 11A is a sectional view of main portions in a normal state. FIG. 11B is a sectional view of main portions in a state where a fluid is discharged. FIG. 11C is a sectional view of main portions showing a manner of sucking a fluid. FIG. 11D is a sectional view of main portions showing another manner of sucking a fluid.

FIG. 12A is a sectional view of main portions in a normal state. FIG. 12B is a sectional view of main portions in a state where a fluid is discharged. FIG. 12C is a sectional view of main portions in a state where a fluid is sucked.

DESCRIPTION OF EMBODIMENTS

Hereinafter, a first embodiment of the medical tube of the invention will be described with reference to FIGS. 1 to 9B.

Figure 1:
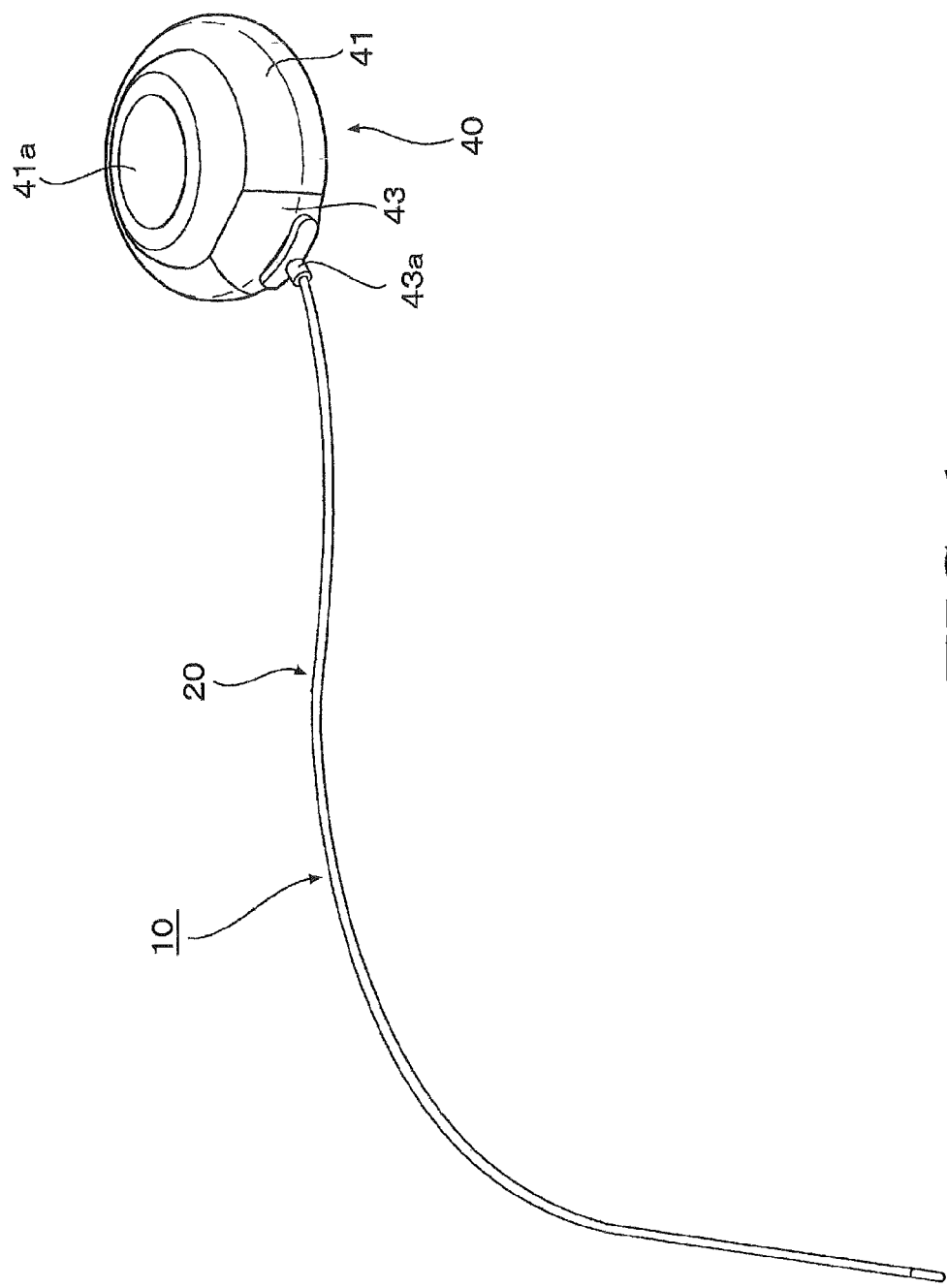
FIG. 1 is a perspective view showing a first embodiment of the medical tube of the invention.

As shown in FIG. 1, the medical tube 10 (hereinafter, referred to as "tube 10") of the embodiment is used as a catheter which is to be inserted into a blood vessel to be indwelled continuously or temporarily in the blood vessel, and which, as required, can administer an anticancer agent, a nutrient, or the like or suck a body fluid such as the blood, or which can discharge and suck a fluid.

Figure 2A:
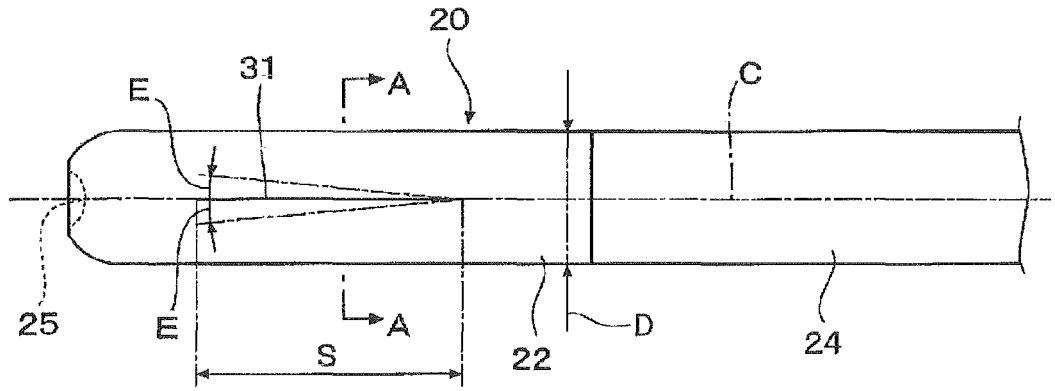
FIGS. 2A to 2C show the medical tube.
Figure 2B:
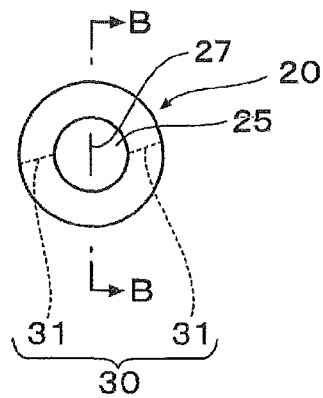
Figure 2C:
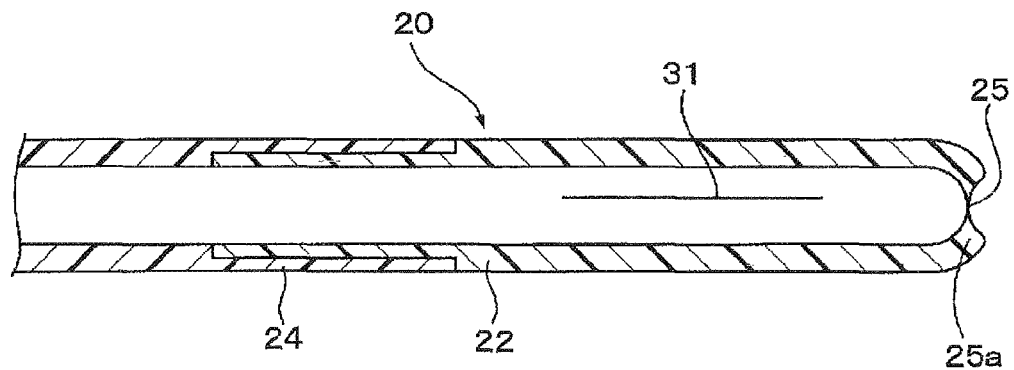

Referring also to FIGS. 2A to 2C, the tube 10 has the cylindrical-tube-shaped main body 20 which extends by a predetermined length, and a valve 30 which is disposed in a portion of the main body 20, the portion being to be inserted into a tubular organ, and which can discharge and suck a fluid.

The tube 10 of the embodiment is configured so that, after indwelled in a predetermined place in the blood vessel, a medical solution injection port 40 is connected to a base end portion of the main body 20 (see FIG. 1). The medical solution injection port 40 is configured by a container 41 which is made of a synthetic resin or the like, and a connecting portion 43 which is detachably attached to a predetermined place of the outer circumference of the container 41. A rubber film 41a through which the needle of a syringe can be pierced is formed in an opening of the upper surface of the container 41. A connection pipe 43a which is connected to the base end portion of the main body 20 is disposed in the connecting portion 43.

The main body 20 is made of a flexible synthetic resin such as nylon, polyethylene, polypropylene, polyvinyl chloride, polyvinyl acetate, polyurethane, polystyrene, polyamide, or silicone, or may be made of a mixture or copolymer thereof. Alternatively, the main body may be made of a fluorine resin such as polytetrafluoroethylene (PTFE), perfluoroalkoxy resin (PFA), tetra-fluoroethylene/hexa-fluoropropylene copolymer (FEP), or ethylene-tetra-fluoroethylene copolymer (ETFE), or a natural rubber.

Among the above-described materials, for example, a material having the hardness, which is specified under JIS K 6253 and measured by a durometer, of 75A to 75D is preferably used, and a material having the hardness of 80A to 93A is more preferably used.

Powder of $BaSO_4$, Bi, W, or the like may be contained in the main body 20 to provide an X-ray opacity. The outer circumference of the main body 20 may be coated by a hydrophilic resin such as 2-methacryloyloxyethyl phosphorylcholine (MPC) polymer, polyvinylpyrrolidone, polyethyleneglycol, or methylvinylether-maleic anhydride copolymer, and further by a physiologically active substance having a fibrinolytic activity, such as urokinase, an antimicrobial agent, pigment/dye (colorant), and the like.

In the embodiment, as shown in FIG. 2C, a tip end wall 25 is provided to close the tip end of the main body 20. The tip end wall 25 is formed so that the middle portion is thin and the peripheral edge 25a of the outer circumference is thick, or has a so-called bowl-like shape (see FIG. 2C). A linear incision 27 is formed in the middle of the tip end wall 25 (see FIG. 2B). The incision 27 normally closes. When a fluid such as an anticancer agent is injected into the main body 20 and the internal pressure is raised, the incision opens to enable the fluid to be discharged. When the interior of the main body 20 is returned to the normal pressure or depressurized, the incision 27 closes, and an external fluid such as the blood is prevented from entering the interior of the main body 20.

Since the bowl-shaped concave is disposed in the tip end wall 25 of the main body 20, and the incision 27 is disposed therein, a guide wire which is not shown can be inserted into the tube 10 through both the tip and base ends of the tube 10. Therefore, the workability in the indwelling of the tube can be improved.

In the tip end wall 25, alternatively, the middle portion may be formed into a spherical shape or a tapered shape. The tip end wall is requested to be formed so that the middle portion is thin and the peripheral edge 25a of the outer circumference is thick. The incision which is formed in the tip end wall 25 may have a Y-like shape, a cross-like shape, or other shapes.

As shown in FIG. 2C, the main body 20 is configured by performing injection molding of a portion 22 in which the tip end wall 25 is disposed, extrusion molding of the other portion 24, and joining of them.

Figure 3:
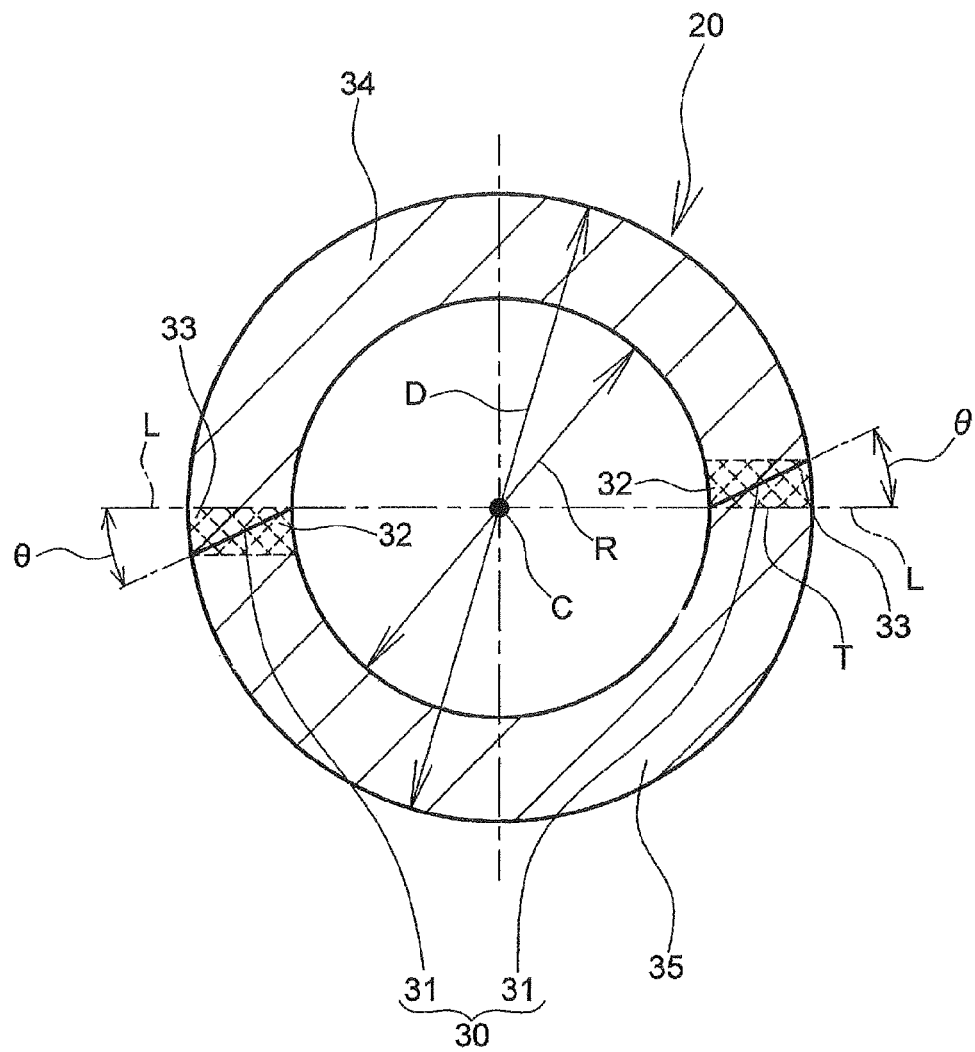
FIG. 3 is an enlarged sectional view where the medical tube is cut along arrow lines A-A in FIG. 2A.

As shown in FIGS. 2A to 2C and 3, the valve 30 in the embodiment is configured by a pair of slits 31, 31 which, in the tip end side of the main body 20, extend by a predetermined length S (see FIG. 2A) in the axial direction of the main body, which are formed so as to extend from the outer circumference of the main body 20 to the inner circumference, and which are opposingly disposed at substantially regular intervals in the circumferential direction of the main body 20 (see FIGS. 2B and 3).

More specifically, in the portion of the main body 20 in which the slits 31 are formed, as viewed in a section perpendicular to the axial center C of the main body 20, as shown in FIG. 3, the slits 31 are formed to be inclined by an angle θ in the same direction with respect to a line L that passes through the axial center C of the main body 20 and that extends in a radial direction. In the embodiment, both the slits 31, 31 are formed so as to be inclined in a counterclockwise direction (left-handed direction) with respect to the line L (see FIG. 3).

As described above, the slits 31, 31 are disposed in the main body 20, and therefore the main body 20 is divided into wall portions 34, 35. The slits 31 are formed to be inclined by the angle θ in the same direction with respect to the line L that passes through the axial center C of the main body 20 and that extends in a radial direction, as described above. Therefore, ones of the end portions which are butted against each other through the slits 31 are formed as inner end portions 32 intersects at an acute angel with the inner circumferential surface, and at an obtuse angle with the outer circumferential surface, and the others of the end portions which are butted against each other through the slits are formed as outer end portions 33 intersects at an obtuse angel with the inner circumferential surface, and at an acute angle with the outer circumferential surface (see the double hatched portions in FIG. 3).

In the invention, the slits 31 are disposed at intervals in the circumferential direction of the main body 20. Preferably, the intervals of the slits 31 are formed so that, as viewed in a section perpendicular to the axial center C of the main body 20, when the outer circumferential length of the predetermined wall portion which is divided by the slits is 1, the outer circumferential length of the remaining wall portion is formed at the ratio of 0.5 to 2.0. More preferably, the outer circumferential length is formed at the ratio of 0.83 to 1.20, and most preferably, at regular intervals.

Figure 4A:
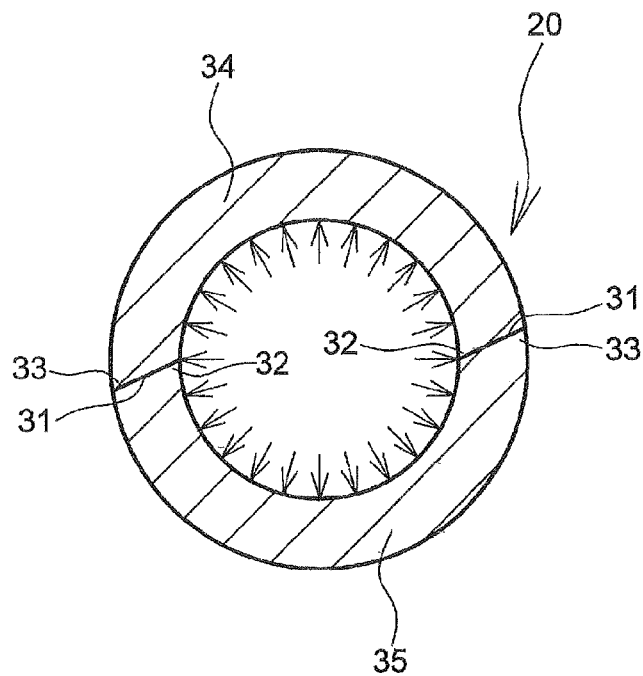
FIGS. 4A and 4B show a state of the medical tube where a fluid is to be discharged to the outside of the tube.
Figure 4B:
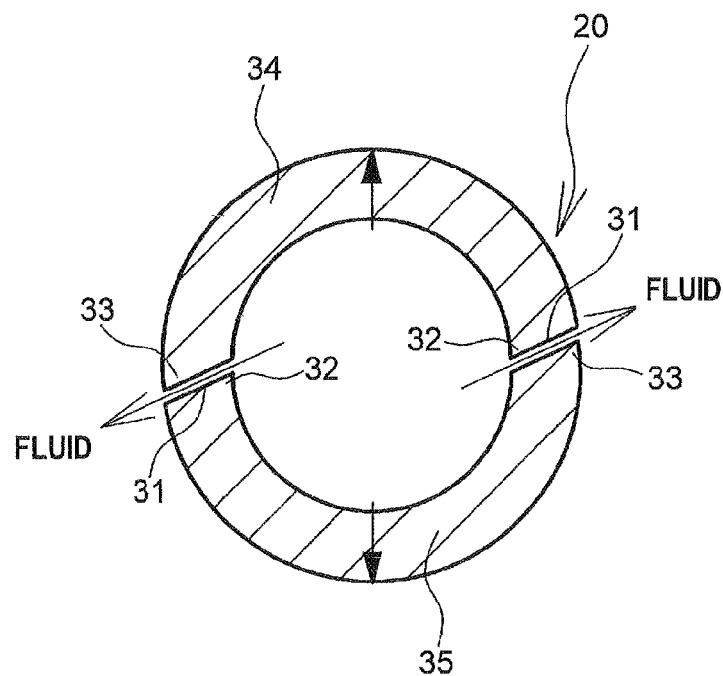
Figure 5:
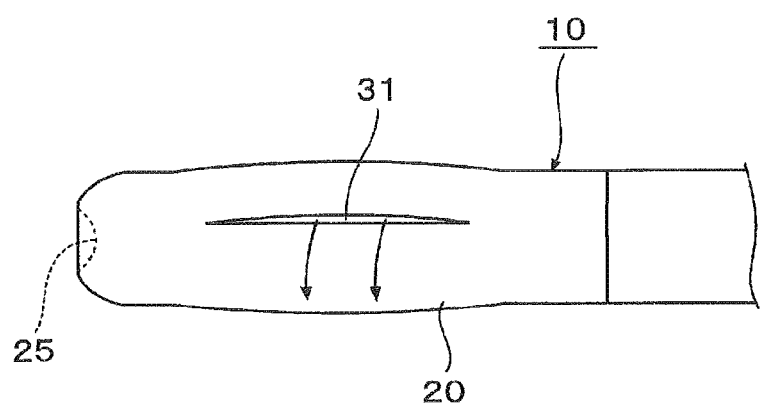
FIG. 5 is a side view of main portions of the medical tube in a state where the slits open, and the fluid is discharged to the outside of the tube.

When a fluid such as an anticancer agent is injected into the main body 20, and the interior is pressurized (see FIG. 4A), the wall portions 34, 35 are pressed toward the outer diameter side of the main body 20, the slits 31, 31 constituting the valve 30 open, and therefore the fluid can be discharged (see FIGS. 4B and 5).

Figure 6A:
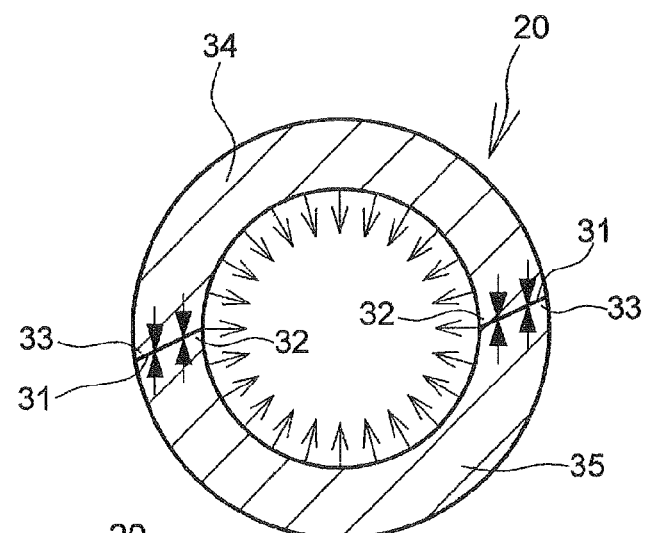
FIGS. 6A to 6C show a state of the medical tube where the fluid is sucked into the tube.

On the other hand, when the interior of the main body 20 is sucked and depressurized, the wall portions 34, 35 bend toward the inner diameter side of the main body 20 by being sucked, and the inner end portions 32 and outer end portions 33 which are butted against each other through the slits 31 of the wall portions 34, 35 are pressed against each other (see FIG. 6A). When the end portions which are butted against each other through the slits 31 are strongly pressed against each other, slippage occurs between the inclined slit surfaces, so that the inner end portions 32 are moved toward the inner diameter side of the main body 20, and the outer end portions 33 are moved toward the outer diameter side of the main body 20 (see FIG. 6B). Therefore, the wall portions 34, 35 which are separated by the plural slits 31 are moved in the inclination direction of the slits 31 (in the direction in which the tip ends of the end portions formed by the slits 31 form an acute angle), the end portions which are butted against each other through the slits 31 are disengaged from each other, and the slits 31 largely open (see FIGS. 6C and 7). Consequently, fluids which exist outside the medical tube, such as a body fluid can be effectively sucked.

Preferably, the angles θ of the slits 31 with respect to the line L of the main body 20 are 10 to 60°, and more preferably 14 to 51°.

Figure 8A:
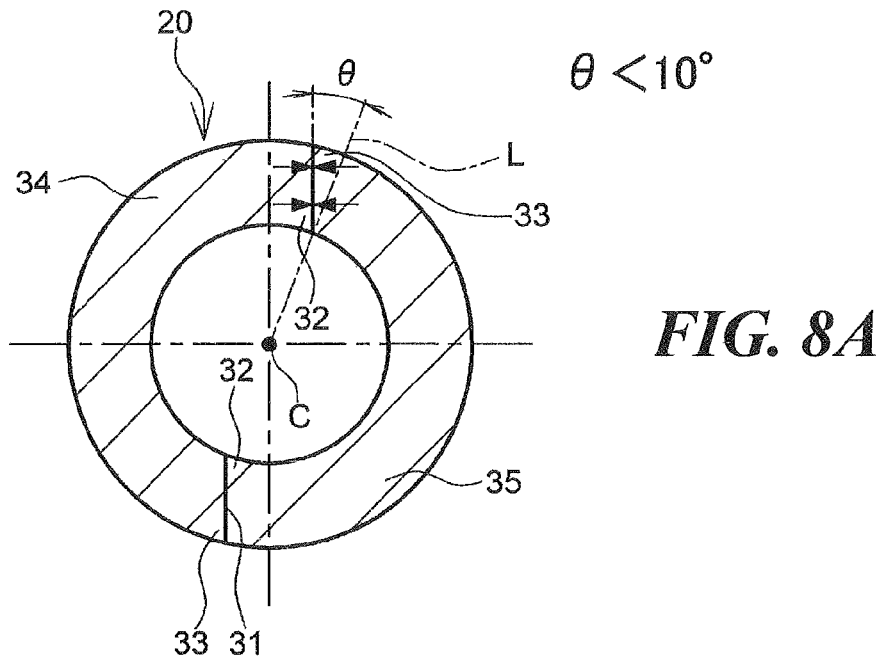
FIGS. 8A and 8B are sectional views of main portions of the medical tube illustrating the difference of the magnitudes of the angles θ of the slits with respect to a line L.
Figure 8B:
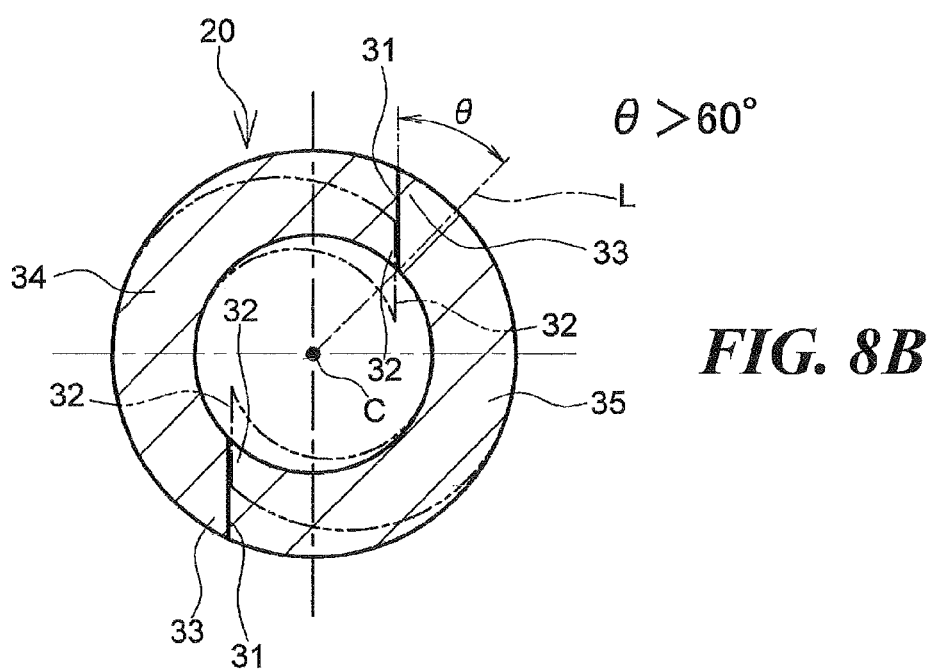

This will be described with reference also to FIGS. 8A and 8B. In the case where the angles θ are smaller than 10°, when the fluid is to be sucked, the opposed end portions 32, 33 of the wall portions 34, 35 are butted against each other to be hardly displaced from each other, and therefore the inner end portions 32 become hard to bend (see FIG. 8A). On the other hand, in the case where the angles θ exceed 60°, when the fluid is to be sucked, although the inner end portions 32 and outer end portions 33 which are butted against each other through the slits 31 may be displaced, the portions are hardly disengaged from each other, and therefore the slits 31 become hard to effectively open (see FIG. 8B). The sectional views of FIGS. 8A and 8B showing the main body 20 are obtained by rotating the main body 20 shown in FIG. 3 by a predetermined angle, and substantially identical therewith (this is applicable also to FIGS. 9A and 9B).

As shown in FIG. 3, when the inner diameter of the main body 20 is R, and the thickness of the main body 20 along the line L is T, preferably, R/T is 2 to 6, and more preferably 2.4 to 4.5.

Figure 9A:
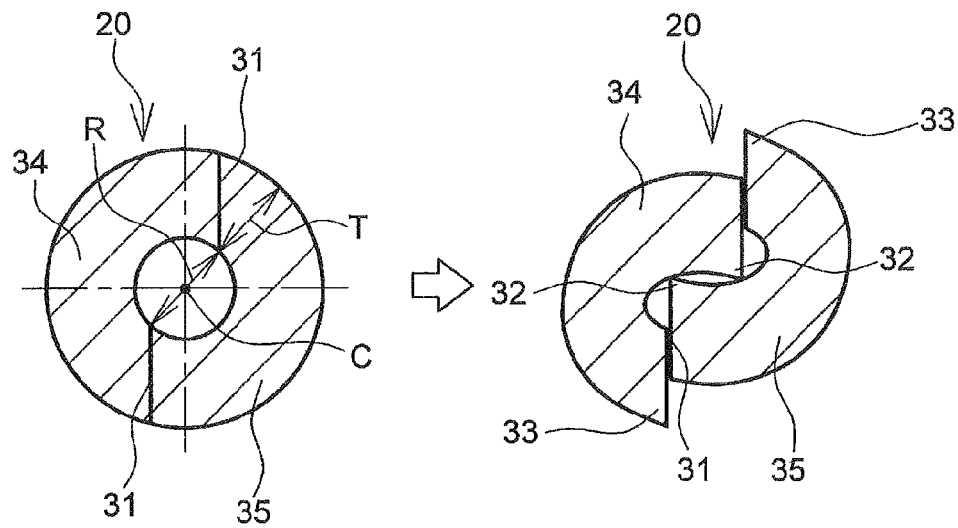
FIGS. 9A and 9B are sectional views of main portions of the medical tube illustrating the difference of the magnitudes of R/T.
Figure 9B:
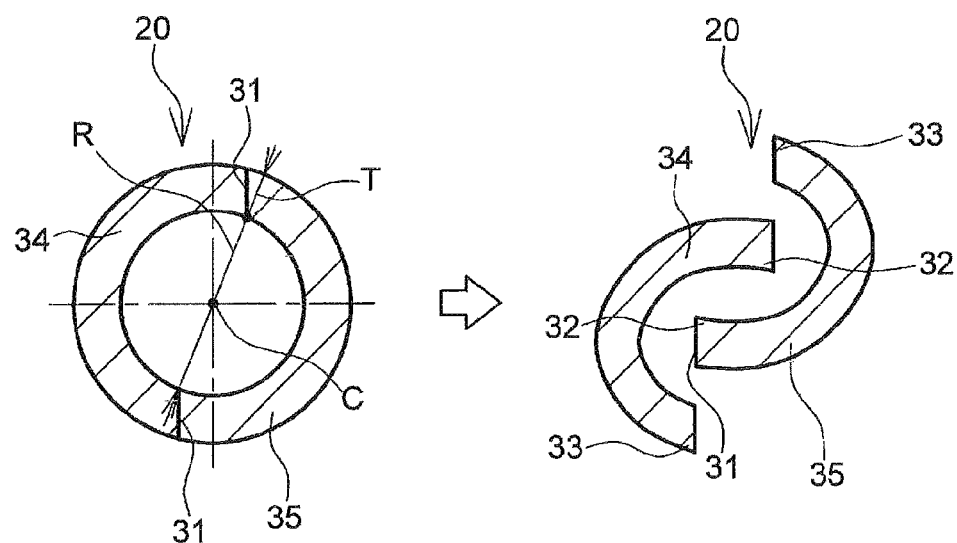

This will be described with reference also to FIGS. 9A and 9B. As shown in FIG. 9A, in the case where R/T above is smaller than 2, even though, when the fluid is to be sucked, the inner end portions 32 and outer end portions 33 which are butted against each other through the slits 31 are displaced, the inner end portions 32 and the outer end portions 33 abut against the inner circumferential surfaces of the opposite wall portions, and are not further positionally displaced. Therefore, the butting end surfaces of the inner end portions 32 and the outer end portions 33 are hardly disengaged from each other, and the slits 31 are effectively caused to hardly open. On the other hand, as shown in FIG. 9B, in the case where R/T above exceeds 6, the slits 31 easily open (see the right figure of FIG. 9B). However, the thickness is smaller than the thicknesses of the tubes shown in FIGS. 1 to 8B, and the thickness of the tube shown in FIG. 9A, and the main body 20 is softened.

As shown in FIG. 2A, preferably, the axial lengths S of the slits 31 are 1.6 to 5.0 times the outer diameter D of the main body 20, and more preferably 2.3 to 3.2 times. In the case where the axial lengths S are less than 1.6 times the outer diameter D of the main body 20, the slits 31 become difficult to open, and the discharging and sucking amounts of the fluid are reduced. On the other hand, in the case where the axial lengths exceed 5.0 times, the rigidity of the main body 20 is lowered, and the closing force in the normal pressure is reduced. Thus, the biological liquid may enter the tube.

In the embodiment, as shown in FIG. 2A, the slits 31 are formed so as be parallel to the axial center C of the main body 20. Alternatively, the slits may be inclined with respect to the axial center C of the main body 20.

As shown in FIG. 2A, preferably, the axial angles E of the slits 31 with respect to the axial center C of the main body 20 are ±6°, and more preferably ±2°. In the case where the angles E are not within the range of ±6°, the circumferential lengths of the wall portions 34, 35 of the main body 20 which are divided by the slits 31 are uneven in the axial direction of the main body 20, deforming operations of the wall portions 34, 35 in the operations of discharging and sucking the fluid are easily dispersed. Thus, there may be caused a variation in the discharging and sucking amounts of the fluid due to the slits 31.

Preferably, a lubricant such as graphite, molybdenum disulfide, a fluorine-containing compound, boron nitride, stearate, or silicone oil may be applied to the mating surfaces of the slits 31. From the viewpoint of the biological compatibility, it is particularly preferable to use silicone oil.

Next, an example of the method of using the thus structured tube 10 will be described. Hereinafter, a case where the tube is used as a blood vessel catheter which is to be inserted and indwelled in a blood vessel to administer a fluid such as an anticancer agent or a nutrient, or to suck the blood will be described.

Firstly, a puncture needle which is not shown is thrust into the blood vessel by the well-known Seldinger technique, and a guide wire which is not shown is introduced from the base end of the puncture needle to be inserted into the blood vessel. Thereafter, the puncture needle is pulled out, and a scabbard-like sheath which is not shown is inserted into the blood vessel along the guide wire. Next, the base end of the guide wire is inserted through the incision 27 of the tip end wall 25 of the tube 10, and the guide wire is introduced into the tube 10. Then, the tip end of the guide wire is placed in a target place in the blood vessel, the tube 10 is inserted into the sheath along the outer circumference of the guide wire, and a tip end portion of the tube is caused to reach the target place in the blood vessel. Thereafter, the guide wire is pulled out from the tube 10, the sheath is pulled out from the blood vessel, the connection pipe 43a of the medical solution injection port 40 is connected to the base end portion of the tube 10, the skin is incised, and the medical solution injection port 40 is embedded under the skin.

In this state, the needle of a syringe which is not shown is pierced through the rubber film 41a of the medical solution injection port 40, and a fluid such as an anticancer agent is injected, whereby the fluid such as an anticancer agent is injected into the main body 20.

Then, the interior of the main body 20 is pressurized by the fluid injected into the main body 20 (see FIG. 4A), and therefore the wall portions 34, 35 which are separated from each other by the slits 31 are pressed toward the outer diameter side of the main body 20. Consequently, the slits 31, 31 constituting the valve 30 open, and therefore the internal fluid of the main body 20 can be discharged to the outside of the main body through the slits 31 (see FIGS. 4B and 5).

In the tube 10, at this time, the fluid can be discharged from the plural slits 31, so that the fluid can be administered in a plural directions to the inner wall of the tubular organ. As a result, the influence of a very powerful medication (anticancer agent or the like) can be mitigated.

In the embodiment, the incision 27 is formed in the tip end wall 25 of the main body 20. In discharging of a fluid, therefore, the slits 31 open as described above, and also the incision 27 which normally closes is caused to open. As a result, the slits 31 and the incision 27 open in discharging of a fluid, and hence the fluid can be smoothly discharged.

Figure 6B:
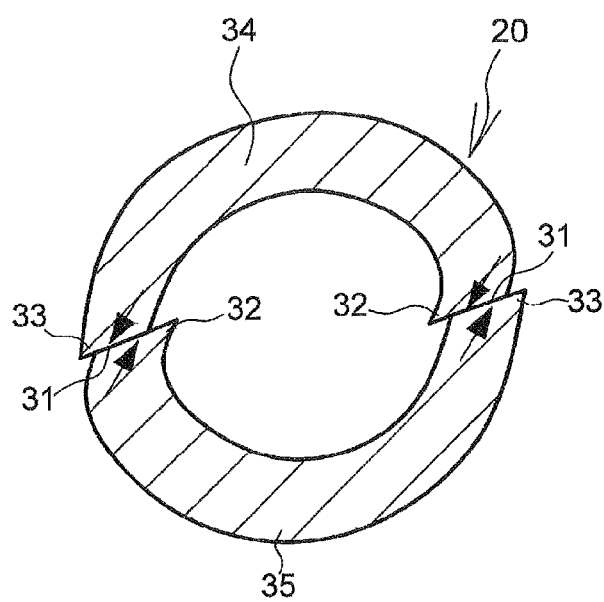
Figure 6C:
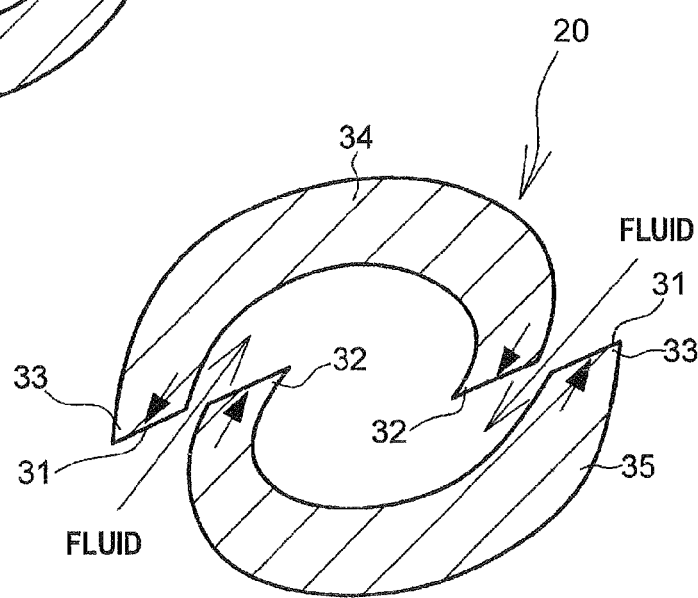
Figure 7:
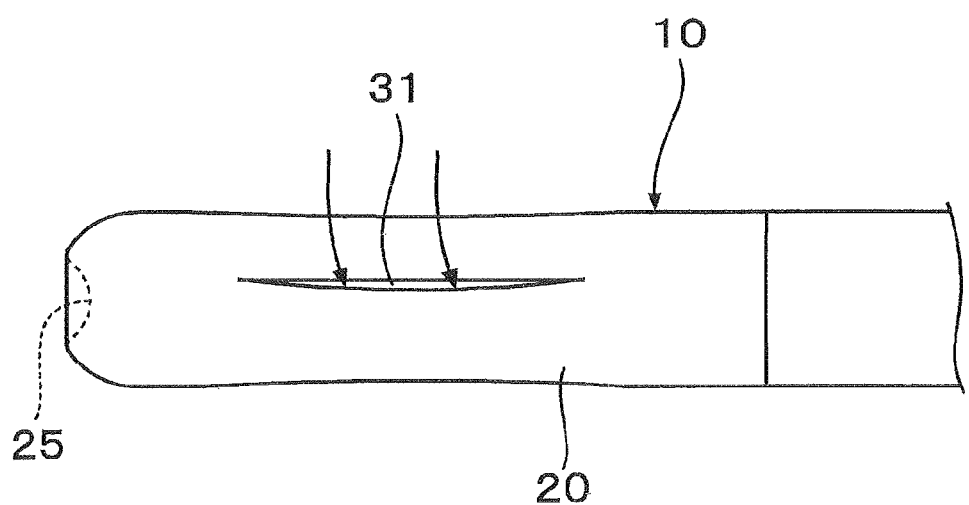
FIG. 7 is a side view of main portions of the medical tube showing a state where the slits open, and the fluid is sucked into the tube.

On the other hand, when a fluid such as the blood is to be sucked by using the tube 10, a pump, syringe, or the like which is not shown is connected to the base end portion of the tube 10, and the device is operated to suck the interior of the main body 20, thereby depressurizing the interior of the tube, As described above, then, the wall portions 34, 35 which are divided by the slits 31 of the main body 20 bend toward the inner diameter side of the main body 20 by being sucked, the inner end portions 32 and outer end portions 33 which are butted against each other through the slits 31 of the wall portions 34, 35 are pressed against each other (see FIG. 6A), slippage occurs between the inclined slit surfaces, the inner end portions 32 are moved toward the inner diameter side of the main body 20, and the outer end portions 33 are moved toward the outer diameter side of the main body 20 (see FIG. 6B). Therefore, the wall portions 34, 35 which are divided by the plural slits 31 are moved in the inclination direction of the slits 31 (in the direction in which the tip ends of the end portions formed by the slits 31 form an acute angle), the end portions which are butted against each other through the slits 31 are disengaged from each other, and the slits 31 largely open (see FIGS. 6C and 7). Consequently, a fluid which exists outside the medical tube, such as a body fluid can be effectively sucked.

In the embodiment, during the operation of sucking a fluid, the incision 27 which is formed in the tip end wall 25 of the main body 20 closes, and therefore the interior of the main body 20 can be effectively depressurized. As a result, the slits 31 are caused to smoothly open, and a fluid on the outside of the main body can be surely sucked.

In the tube 10, when the interior of the main body 20 is depressurized, the plural slits 31 open as described above. In the case where the main body 20 of the tube 10 is inserted into a tubular organ such as a blood vessel, even when a circumferential part of the main body 20 abuts against the inner wall of the tubular organ, and the slit 31 in the part is closed, therefore, the other slit 31 can be maintained in a state where the slit opens, and the fluid can be surely sucked into the main body 20.

The plural slits 31 are disposed at intervals in the circumferential direction of the main body 20. In the above-described operation of discharging a fluid, therefore, the pressing force caused by the fluid acts in a balanced manner on the inner surfaces of the wall portions 34, 35 (see FIG. 4A). Also, in the operation of sucking a fluid, the suction force caused by a pump, a syringe, or the like acts in a balanced manner on the inner surfaces of the wall portions 34, 35 (see FIG. 6A). In the operations of discharging or sucking a fluid, consequently, the wall portions 34, 35 are caused to easily deform, and the slits 31 are enabled to easily open (see FIGS. 4B and 6B). Since the plural slits 31 are disposed in the main body 20, the discharging and sucking amounts can be increased in the operations of discharging and sucking a fluid.

In the case where the angles θ of the slits 31 with respect to the line L of the main body 20 are set to 10 to 60°, the oblique slits 31 which are inclined by the angle θ with respect to the line L allow the portions of the inner end portions 32 and the outer end portions 33 where the wall portions 34, 35 overlap with each other in the direction of the line L to have an adequate area. Thus, when the suction force caused by a pump, a syringe, or the like acts on the interior of the main body, the slits 31 can be therefore caused to easily open.

Assuming a case where the inner diameter of the main body 20 is R, the thickness of the main body 20 along the line L is T, and R/T is 2 to 6, when the interior of the main body is sucked by a pump, a syringe, or the like, and the inner end portions 32 of the wall portions 34, 35 of the main body 20 bendingly deform toward the inner diameter side, the inner end portions 32 and the outer end portions 33 are completely displaced from each other, and the slits 31 can be caused to easily open.

In the case where the axial lengths S of the slits 31 are 1.6 to 5.0 times the outer diameter D of the main body, the suction performance due to the slits 31 can be enhanced, while the rigidity of the main body 20 is maintained.

In the case where the axial angles E of the slits 31 with respect to the axial center C of the main body 20 are ±6°, the circumferential lengths of the wall portions 34, 35 of the main body 20 which are separated by the slits 31 can be made substantially even in the axial direction of the main body 20, and therefore the deforming operations of the wall portions 34, 35 in the operations of discharging and sucking a fluid are allowed to be performed in a balanced manner.

In the case where a lubricant is applied to the mating surfaces of the slits 31, it is possible to reduce the friction resistances of the contact surfaces between the inner end portions 32 and outer end portions 33 which are opposed to each other in the wall portions 34, 35 that are separated from each other by the slits 31. When the interior of the main body 20 is depressurized, therefore, the inner end portions 32 can be easily displaced toward the inner diameter side of the main body, and the slits 31 are enabled to easily open.

Although it has been described that the tube 10 of the embodiment is used as a catheter which is to be inserted into a blood vessel, the invention may be applied also to a medical tube which is used by being inserted into a tubular organ of the human body, such as the ureter, the bile duct, the trachea, or the like, for example, a shunt tube for, in treatment of hydrocephalus or the like, draining a fluid accumulated in the brain ventricle into the abdominal cavity, and a drainage tube which is used for draining the bile accumulated in the bile duct.

Figure 10A:
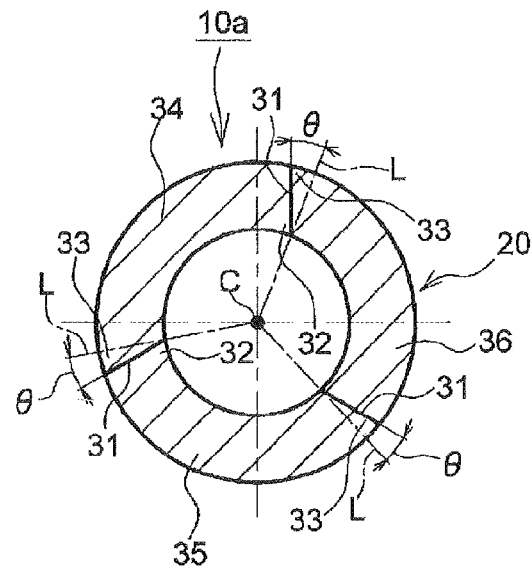
FIGS. 10A to 10C show a second embodiment of the medical tube of the invention.
Figure 10B:
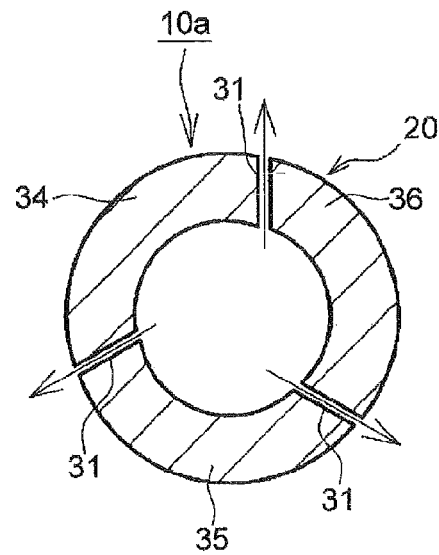
Figure 10C:
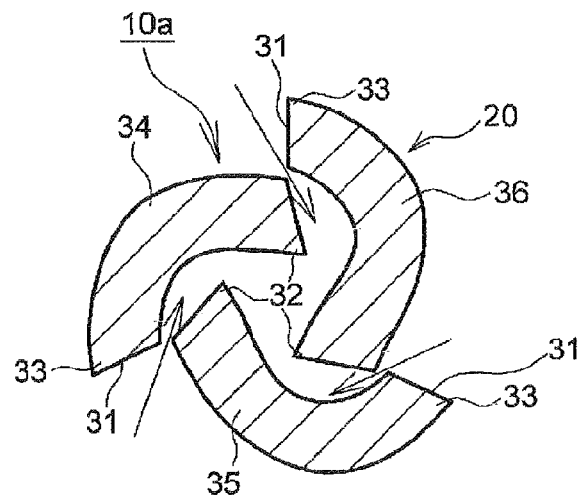

FIGS. 10A to 10C show a second embodiment of the medical tube of the invention. The portions which are substantially identical with those in the above-described embodiment are denoted by the same reference numerals, and their description is omitted.

In the medical tube 10a (hereinafter, referred to as "tube 10a") of the embodiment, as shown FIG. 10A, three slits 31 are disposed at substantially regular intervals in the circumferential direction of the main body 20, as viewing a portion where the slits 31 of the main body 20 are formed, in a section perpendicular to the axial center C of the main body 20. Therefore, three wall portions 34, 35, 36 are formed. The slits 31 are formed so as to be inclined by the angle θ in the same direction (counterclockwise direction) with respect to the line L which passes through the axial center C of the main body 20, and which extends in a radial direction.

Also in the tube 10a of the embodiment, when a fluid is injected into the main body 20, and the interior is pressurized, the wall portions 34, 35, 36 are pressed toward the outer diameter side of the main body 20, the slits 31 open, and therefore the fluid can be discharged (see FIG. 10B). On the other hand, when the interior of the main body 20 is sucked and depressurized, the inner end portions 32 of the wall portions receive a suction force which is greater than that applied to the outer end portions 33 of the respective wall portions, the inner end portions 32 bend so as to be displaced toward the inner diameter side with respect to the outer end portions 33, the slits 31 open, and a fluid on the outside of the main body can be sucked into the main body 20 (FIG. 10C).

FIGS. 11A to 11D show a third embodiment of the medical tube of the invention. The portions which are substantially identical with those in the above-described embodiments are denoted by the same reference numerals, and their description is omitted.

Figure 11A:
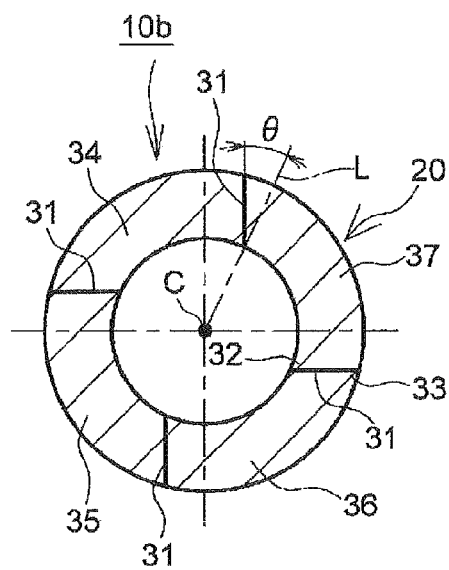
FIGS. 11A to 11D show a third embodiment of the medical tube of the invention.

In the medical tube 10b (hereinafter, referred to as "tube 10b") of the embodiment, as shown FIG. 11A, four slits 31 are disposed at substantially regular intervals in the circumferential direction of the main body 20, as viewing a portion where the slits 31 of the main body 20 are formed, in a section perpendicular to the axial center C of the main body 20. Therefore, four wall portions 34 to 37 are formed. The slits 31 are formed so as to be inclined by the angle θ in the same direction (counterclockwise direction) with respect to the line L which passes through the axial center C of the main body 20, and which extends in a radial direction.

Figure 11B:
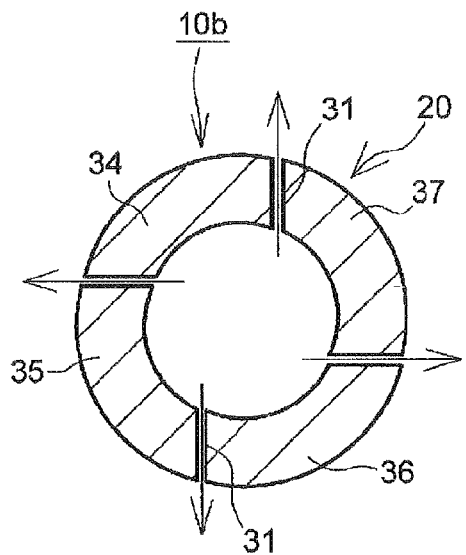

In the tube 10b of the embodiment, when a fluid is injected into the main body 20, and the interior is pressurized, the wall portions 34, 35, 36, 37 are pressed toward the outer diameter side of the main body 20, the four slits 31 open, and therefore the fluid can be discharged (see FIG. 11B).

Figure 11C:
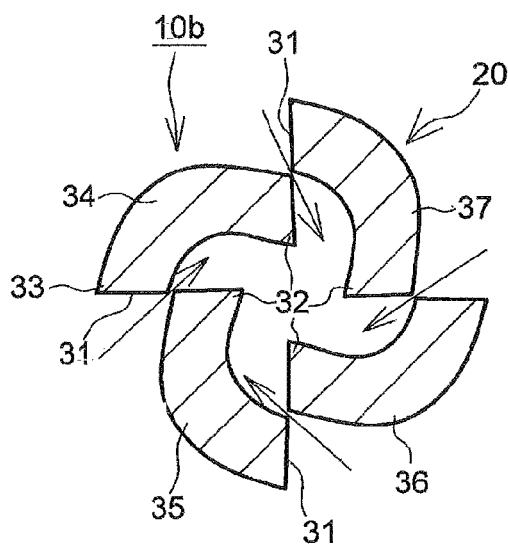
Figure 11D:
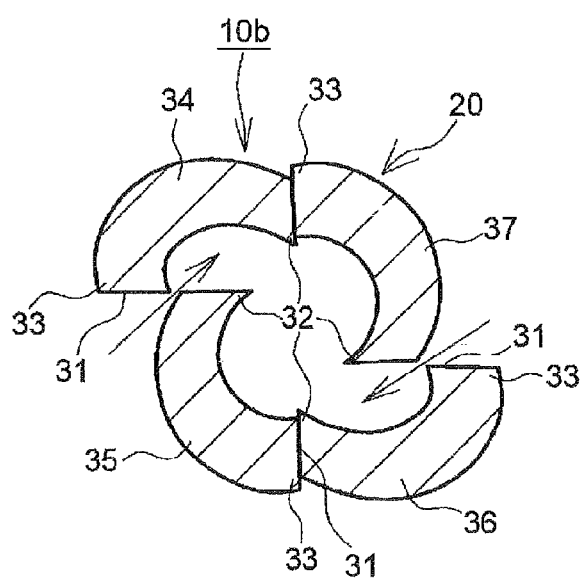

On the other hand, when the interior of the main body 20 is sucked and depressurized, the wall portions bendingly deform as shown in FIG. 11C or FIG. 11D. This change seems to occur in accordance with the above described R/T ratio of the tube 10b, the axial lengths S of the slits 31, and the like.

In the case shown in FIG. 11C, namely, the inner end portions 32 of the wall portions receive a suction force which is greater than that applied to the outer end portions 33 of the other wall portions, the inner end portions 32 bend so as to be displaced toward the inner diameter side with respect to the outer end portions 33, the four slits 31 open, and a fluid on the outside of the main body can be sucked into the main body 20.

On the other hand, in the case shown in FIG. 11D, when the wall portions bendingly deform, the inner end portion(s) 32 and outer end portion(s) 33 of a part of the wall portions abut against each other, and the slit(s) therebetween close(s). However, the configuration where the slits 31 are formed so as to be inclined by the angle θ in the same direction with respect to the line L which passes through the axial center C of the main body 20, and which extends in a radial direction prevents a situation where all the end portions 32, 33 collide with each other, from occurring. Therefore, either of the slits 31 can be caused to open, and a fluid on the outside of the main body can be sucked.

Figure 12A:
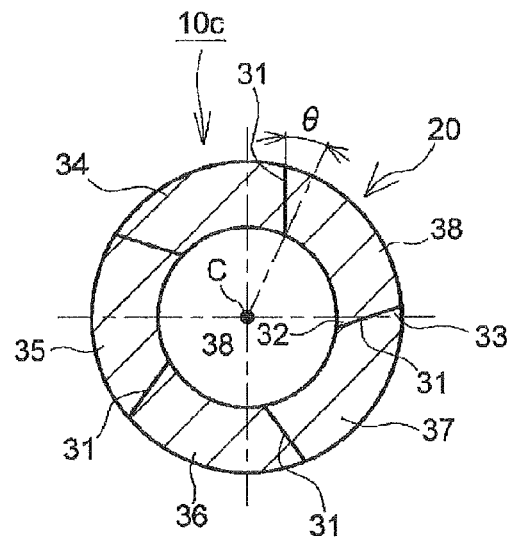
FIGS. 12A to 12C shows a fourth embodiment of the medical tube of the invention.
Figure 12B:
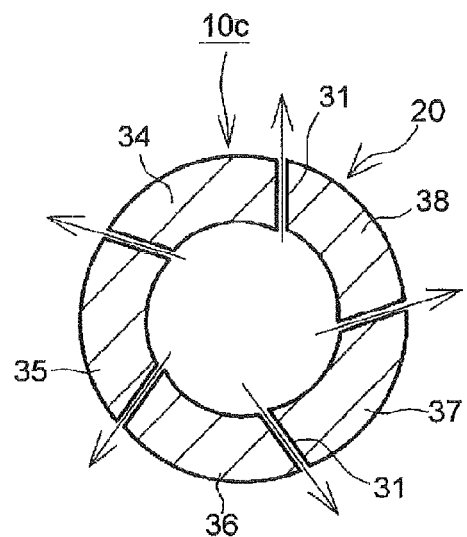
Figure 12C:
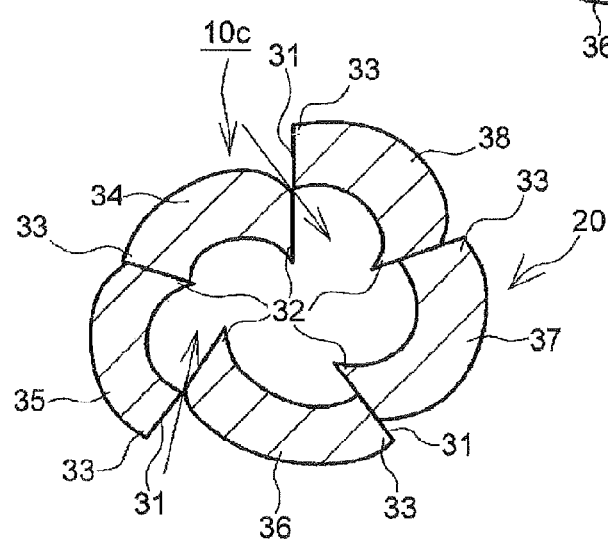

FIGS. 12A to 12C show a fourth embodiment of the medical tube of the invention. The portions which are substantially identical with those in the above-described embodiments are denoted by the same reference numerals, and their description is omitted.

In the medical tube 10c (hereinafter, referred to as "tube 10c") of the embodiment, as shown FIG. 12A, five slits 31 are disposed at substantially regular intervals in the circumferential direction of the main body 20, as viewing a portion where the slits 31 of the main body 20 are formed, in a section perpendicular to the axial center C of the main body 20. Therefore, five wall portions 34 to 38 are formed. The slits 31 are formed so as to be inclined by the angle θ in the same direction (counterclockwise direction) with respect to the line L which passes through the axial center C of the main body 20, and which extends in a radial direction.

In the tube 10c of the embodiment, when a fluid is injected into the main body 20, and the interior is pressurized, the wall portions 34 to 38 are pressed toward the outer diameter side of the main body 20, the five slits 31 open, and therefore the fluid can be discharged (see FIG. 12B).

On the other hand, when the interior of the main body 20 is sucked and depressurized, the inner end portions 32 and outer end portions 33 of predetermined one(s) of the wall portions abut against each other, and the slit(s) therebetween close(s) as shown in FIG. 12C. However, a fluid on the outside of the main body can be sucked through the other slit(s) which open.

In the above-described embodiments, 2 to 5 slits are disposed at regular intervals in the circumferential direction of the main body constituting the medical tube. Alternatively, a larger number of slits may be disposed. In the case where the number of slits is increased, when an unintended external force is applied to the valve during the indwelling of the tube, however, the tube is easily deformed, and therefore the slits are caused to easily open. Consequently, the number of slits is preferably 2 to 4, and particularly preferably 2.

Examples

The fluid suction performance was checked with respect to medical tubes including a vale similar to that of the invention.

1. Suction Test 1

(1) Preparation of Samples

Tubes of the dimensions and materials shown in Table 1 below were cut to a predetermined length to form the main bodies 20, and slits 31, 31 which are inclined by 30° in the same direction with respect to the line L that passes through their axial center C of the main body were formed at regular intervals in the circumferential direction, whereby medical tubes of Samples 1 to 9 were prepared. The slits 31 were formed while setting the axial lengths S to 5 mm.

(2) Testing Method

A lubricant made of silicone was applied to the mating surfaces of the slits 31 of Samples 1 to 9, syringes were connected to the base end portions of the respective samples, the samples were inserted into a container in which a predetermined fluid was accumulated, and suctions were performed at a predetermined pressure by using the syringes, and the fluid suction performances were checked. Table 1 below shows results of the above. In Table 1, "WW" means that the suction performance was very excellent, "XX" means that the suction was excellent, and "ZZ" means that suction was impossible.

(3) Test Results

As a result, it was confirmed that, when R/T is high, the suction performance is excellent (see Table 1).

TABLE 1

| | Material | Inner Diameter R (mm) | Outer Diameter D (mm) | Thickness T (mm) | R/T | Suction Performance |
|---|---|---|---|---|---|---|
| Sample 1 | Urethane | 1.12 | 1.91 | 0.40 | 2.84 | WW |
| Sample 2 | | 1.24 | 2.03 | 0.40 | 3.14 | WW |
| Sample 3 | | 1.29 | 1.98 | 0.35 | 3.74 | WW |

TABLE 1-continued

| | Material | Inner Diameter R (mm) | Outer Diameter D (mm) | Thickness T (mm) | R/T | Suction Performance |
|---|---|---|---|---|---|---|
| Sample 4 | | 1.34 | 1.93 | 0.30 | 4.54 | WW |
| Sample 5 | Silicone | 2.30 | 5.50 | 1.60 | 1.44 | ZZ |
| Sample 6 | | 1.00 | 2.00 | 0.50 | 2.00 | XX |
| Sample 7 | | 1.20 | 2.20 | 0.50 | 2.40 | WW |
| Sample 8 | | 1.50 | 2.50 | 0.50 | 3.00 | WW |
| Sample 9 | | 6.00 | 8.00 | 1.00 | 6.00 | XX |

WW: Suction was very excellent
XX: Suction was excellent
ZZ: Suction was impossible 2. Suction Test 2

(1) Preparation of Samples

Tubes in which the axial lengths S of the slits 31 were set to 3 mm, 4 mm, 5 mm, 6 mm, 7 mm, 8 mm, 9 mm, and 10 mm were prepared with respect to Samples 1 to 9 above (see Table 2). Table 2 shows also S/D of each sample.

(2) Testing Method

A lubricant made of silicone was applied to the mating surfaces of the slits 31 of Samples 1 to 9, and a suction test was performed by the same method as that in Suction test 1 above. Table 2 below shows results of the above. In Table 2, "WW" means that the suction performance was very excellent, "XX" means that the suction was excellent, "YY" means that the suction was not sufficient, and "ZZ" means that suction was impossible.

(3) Test Results

As a result, it was confirmed that tubes in which the axial lengths S of the slits 31 are large with respect to the outer diameter D of the tube main body tend to exhibit superior suction performance (see Table 2).

test 1 above. Table 3 below shows results of the above. In Table 3, "XX" means that the suction was excellent, and "YY" means that the suction was not sufficient.

(3) Test Results

As a result, it was confirmed that, in all Sample Nos. 1 to 7, the suction performance is excellent (see Table 3).

TABLE 3

| Sample No. | Angle X1 (°) | Angle X2 (°) | Average Angle (°) | Suction performance |
|---|---|---|---|---|
| 1 | 15 | 15 | 15 | XX |
| 2 | 19 | 26 | 23 | XX |
| 3 | 20 | 20 | 20 | XX |
| 4 | 30 | 30 | 30 | XX |
| 5 | 31 | 43 | 37 | XX |
| 6 | 36 | 47 | 42 | XX |
| 7 | 48 | 48 | 48 | XX |

WW: Suction was very excellent
YY: Suction was not sufficient

REFERENCE SIGNS LIST 10, 10a, 10b, 10c medical tube (tube)
20 main body
30 valve
31 slit
32 inner end portion
33 outer end portion
34, 35, 36 wall portion
C axial center of main body
D outer diameter of main body
E axial angles of slit
L line

TABLE 2

| | | | S/D, Suction performance | | | | | | | | | | | | | | |
|---|---|---|---|---|---|---|---|---|---|---|---|---|---|---|---|---|---|
| | Material | R/T | S: 3 mm | | S: 4 mm | | S: 5 mm | | S: 6 mm | | S: 7 mm | | S: 8 mm | | S: 9 mm | | S: 10 mm | |
| Sample 1 | Urethane | 2.84 | 1.58 | ZZ | 2.11 | XX | 2.63 | WW | 3.16 | WW | 3.68 | XX | 4.21 | XX | 4.71 | XX | 5.24 | XX |
| Sample 2 | | 3.14 | 1.52 | ZZ | 2.02 | XX | 2.53 | WW | 3.03 | WW | 3.54 | XX | 4.04 | XX | 4.43 | XX | 4.93 | XX |
| Sample 3 | | 3.74 | 1.48 | ZZ | 1.97 | XX | 2.46 | WW | 2.96 | WW | 3.45 | XX | 3.94 | XX | 4.55 | XX | 5.05 | XX |
| Sample 4 | | 4.54 | 1.55 | ZZ | 2.07 | XX | 2.59 | WW | 3.11 | WW | 3.63 | XX | 4.15 | XX | 4.66 | XX | 5.18 | XX |
| Sample 5 | Silicone | 1.44 | 0.55 | ZZ | 0.73 | ZZ | 0.91 | ZZ | 1.09 | ZZ | 1.27 | ZZ | 1.45 | YY | 1.64 | XX | 1.82 | XX |
| Sample 6 | | 2.00 | 1.50 | ZZ | 2.00 | XX | 2.50 | XX | 3.00 | XX | 3.50 | XX | 4.00 | XX | 4.50 | XX | 5.00 | XX |
| Sample 7 | | 2.40 | 1.36 | ZZ | 1.82 | XX | 2.27 | WW | 2.73 | WW | 3.18 | XX | 3.64 | XX | 4.09 | XX | 4.55 | XX |
| Sample 8 | | 3.00 | 1.20 | ZZ | 1.60 | XX | 2.00 | WW | 2.40 | WW | 2.80 | XX | 3.20 | XX | 3.60 | XX | 4.00 | XX |
| Sample 9 | | 6.00 | 0.38 | ZZ | 0.50 | XX | 0.63 | XX | 0.75 | XX | 0.88 | XX | 1.00 | XX | 1.13 | XX | 1.25 | XX |

WW: Suction was very excellent
XX: Suction was excellent
YY: Suction was not sufficient
ZZ: Suction was impossible 3. Suction Test 3

(1) Preparation of Samples

Sample Nos. 1 to 7 were prepared with respect to a medical tube having the material, inner diameter R, outer diameter D, and thickness T which are identical with those of Sample 1 in Suction test 1 above, while setting the angles θ of the two slits 31, 31 with respect to the line L of the main body 20, to the angles (°) shown in Table 3 below. In Table 3, Angle X1 means the angle θ in the right portion of FIG. 3, and Angle X2 means the angle θ in the left portion of FIG. 3. In all the slits 31, the axial length S is 5 mm.

(2) Testing Method

A lubricant made of silicone was applied to the mating surfaces of the slits 31 of Sample Nos. 1 to 7, and a suction test was performed by the same method as that in Suction θ angle of slit with respect to line L
S axial length of slit

The invention claimed is:

1. A medical tube which is to be inserted into a tubular organ or a body cavity to discharge or suck a fluid, including:
a tubular main body which extends by a predetermined length in which a single internal passage is defined; and
a valve which is disposed in a portion of the main body, the portion being to be inserted into the tubular organ or the body cavity, and which is configured to discharge or suck the fluid,
wherein the valve is configured by plural slits which extend by a predetermined length in an axial direction of the main body, which are formed so as to extend from an outer circumference of the main body to an inner circumference, and which are disposed at intervals in a circumferential direction of the main body, wherein the portion of the main body in which the valve is disposed is divided into plural wall portions by providing the plural slits, wherein the slits are formed to be inclined in a same direction with respect to a line L that passes through an axial center C of the main body and that extends in a radial direction, wherein axial angles E of the slits with respect to the axial center C of the main body are ±6°, and wherein the slits are configured to open when the fluid is injected into the main body and an interior thereof is pressurized, and to open through a slippage occurred between inclined slit surfaces when the interior of the main body is sucked and the interior of the main body is depressurized.

2. The medical tube of claim 1, wherein the main body is made of a flexible synthetic resin, a fluorine resin, or a natural rubber, which has a hardness of 75A to 75D measured by a durometer, wherein angles θ of the slits with respect to the line L of the main body are 10 to 60°, wherein R/T is 2 to 6, where an inner diameter of the main body is R and a thickness of the main body along the line L is T, and wherein axial lengths S of the slits are 1.6 to 5.0 times an outer diameter D of the main body.

3. The medical tube of claim 1, wherein a lubricant is applied to mating surfaces of the slits.

* * * * *